US012650417B2

(12) United States Patent
Wu et al.

(10) Patent No.: US 12,650,417 B2
(45) Date of Patent: Jun. 9, 2026

(54) APPARATUS, SYSTEM, SENSOR AND METHOD FOR DETERMINING DISSOLVED OXYGEN CONTENT IN A MEDIUM

(71) Applicants: The Education University of Hong Kong, Hong Kong (HK); The City University of Hong Kong, Hong Kong (HK); Shiu Sun Wu, Hong Kong (HK); Arul Lenus Roy Vellaisamy, Hong Kong (HK); Man Ying Chiu, Hong Kong (HK)

(72) Inventors: Shiu Sun Wu, Hong Kong (HK); Chi Chiu Ko, Hong Kong (HK); Arul Lenus Roy Vellaisamy, Hong Kong (HK); Man Ying Chiu, Hong Kong (HK)

(73) Assignees: Shiu Sun Wu, Hong Kong (HK); Arul Lenus Roy Vellaisamy, Hong Kong (HK); Man Ying Chiu, Hong Kong (HK); The Education University of Hong Kong, Hong Kong (HK); The City University of Hong Kong, Hong Kong (HK)

( * ) Notice: Subject to any disclaimer, the term of this patent is extended or adjusted under 35 U.S.C. 154(b) by 150 days.

(21) Appl. No.: 17/341,686

(22) Filed: Jun. 8, 2021

(65) Prior Publication Data

US 2022/0390427 A1 Dec. 8, 2022

(51) Int. Cl.

*G01N 21/01* (2006.01)
*B01L 3/00* (2006.01)

(Continued)

(52) U.S. Cl.

CPC .............. *G01N 33/18* (2013.01); *B01L 3/508* (2013.01); *C09K 9/02* (2013.01); *C09K 11/07* (2013.01);

(Continued)

(58) Field of Classification Search

CPC ............... G01N 33/1806; G01N 33/18; G01N 21/6428; G01N 27/02; G01N 27/305;

(Continued)

(56) References Cited

U.S. PATENT DOCUMENTS

| | | | |
|---|---|---|---|
| 2,913,386 | A | 11/1959 | Clark, Jr. |
| 9,541,539 | B2 | 1/2017 | Machuca et al. |

(Continued)

FOREIGN PATENT DOCUMENTS

| | | | |
|---|---|---|---|
| CN | 208872741 U | | 5/2019 |
| DE | 102019116397 A1 | * | 12/2020 |

OTHER PUBLICATIONS

Cao, Youfu, Yong-Eun Lee Koo, Sang Man Koo, and Raoul Kopelman. "Ratiometric singlet oxygen nano-optodes and their use for monitoring photodynamic therapy nanoplatforms." Photochemistry and photobiology 81, No. 6 (2005): 1489-1498. (Year: 2005).*

(Continued)

*Primary Examiner* — Rebecca M Fritchman

(74) *Attorney, Agent, or Firm* — FASKEN MARTINEAU DUMOULIN LLP; Kimberly A Peaslee

(57) ABSTRACT

An apparatus, a system, sensor, and a method for determining dissolved oxygen content in air and aqueous medium are disclosed herein. The dissolved oxygen content may be determined by irradiating the sensor comprising at least a photo-oxidizable compound by a light irradiation source, wherein the irradiation enables the photo-oxidizable compound to change its luminescent properties based upon photo-oxidation thereby enabling the quantification of the (Continued)

dissolved oxygen content in the medium. The dissolved oxygen content may be captured via the impedance response generated by interdigitated conducting electrode patterns included in the sensor. The dissolved oxygen content registered by the interdigitated conducting electrode patterns may be transmitted to a user device via a short range or long-range communication via an electronic circuit embedded within the sensor.

7 Claims, 8 Drawing Sheets

(51) Int. Cl.

| | |
|---|---|
| ***C09K 9/02*** | (2006.01) |
| ***C09K 11/07*** | (2006.01) |
| ***G01N 21/64*** | (2006.01) |
| ***G01N 27/02*** | (2006.01) |
| ***G01N 27/30*** | (2006.01) |
| ***G01N 33/18*** | (2006.01) |
| *H04W 88/02* | (2009.01) |

(52) U.S. Cl.
CPC ......... *G01N 21/6428* (2013.01); *G01N 27/02* (2013.01); *G01N 27/305* (2013.01); *B01L 2200/12* (2013.01); *B01L 2300/023* (2013.01); *B01L 2300/0645* (2013.01); *B01L 2300/0663* (2013.01); *C09K 2211/1011* (2013.01); *G01N 33/1806* (2013.01); *H04W 88/02* (2013.01)

(58) Field of Classification Search
CPC .... G01N 21/01; G01N 21/3103; G01N 27/26; G01N 27/30; B01L 3/508; B01L 2200/12; B01L 2300/023; B01L 2300/0645; B01L 2300/0663; C09K 9/02; C09K 11/07; C09K 2211/1011; H04W 88/02
See application file for complete search history.

(56) References Cited

U.S. PATENT DOCUMENTS

| | | | | |
|---|---|---|---|---|
| 2006/0240558 | A1* | 10/2006 | Zhao | G01N 33/1806 436/62 |
| 2019/0040351 | A1* | 2/2019 | Burge | C12M 41/46 |
| 2019/0174210 | A1* | 6/2019 | Robl | H04Q 9/02 |

OTHER PUBLICATIONS

Machine Translation DE 102019116397 A1 (Year: 2020).*
Kuznetsova et al (The photochemistry of coumarins, Russian Chemical Reviews, 61 (7), 1992, pp. 683-696) (Year: 1992).*
Gunther in On the use of 9,10-dimethylanthracene as chemical rate constant actinometer in singlet molecular oxygen reactions ( Year: 2000).*
Search report of counterpart European Patent Application No. 21179728.7 issued on Nov. 29, 2021.
Li Meng et al., Improved Potentiometric and Optic Sensitivity of Polyaniline Film to Dissolved Oxygen by Incorporating Iron-Porphyrin, Electroanalysis, Jun. 1, 2015, pp. 1427-1435, vol. 27, No. 6.
Bencsik Gabor et al., Photo-electrochemical Sensor for Dissolved Oxygen, Based on a Poly(3,4-Ethylenedioxythiophene)/Iron Oxalate Hybrid Electrode, Analyst, Jan. 1, 2010, pp. 375-380, vol. 135, No. 2.
Xu-Dong Wang et al., Optical Methods for Sensing and Imaging Oxygen: Materials, Spectroscopies and Applications, Chemical Society Reviews, Jan. 1, 2014, pp. 3666-3761, vol. 43, No. 10.
Christopher S. Foote, Photosensitized Oxygenations and the Role of Singlet Oxygen, Accounts of Chemical Research, Apr. 1968, 104-110, vol. 1.

* cited by examiner

APPARATUS, SYSTEM, SENSOR AND METHOD FOR DETERMINING DISSOLVED OXYGEN CONTENT IN A MEDIUM

TECHNICAL FIELD

The present application described herein, in general, relates to an apparatus, a system, a sensing device and a method for measuring dissolved oxygen in a medium. More particularly, the present disclosure describes a sensing device, i.e., oxygen sensor for measuring dissolved oxygen in a medium based on chemical products produced by photo-oxidation.

BACKGROUND

Dissolved oxygen (hereinafter may be interchangeably referred to as ("DO") is an important environmental parameter commonly measured in water and air quality monitoring, environmental management and regulatory compliance, pollution control, aquaculture, wastewater treatment processes/discharges and environmental impact assessment.

One of the known existing methods of determining DO is the wrinkle titration method. In this method, aqueous samples are treated with manganous sulfate, potassium hydroxide, and potassium iodide to form manganous hydroxide, $Mn(OH)_2$ which oxidize potassium iodide to form manganous hydroxide, $Mn(OH)_2$ which oxidize potassium iodide into free iodine in proportion to dissolved oxygen in the sample. The wrinkle titration method is subject to numerous interferences such as the presence of nitrite ion, ferrous and ferric iron, suspended solids, and organic matter. This method overestimates and underestimates DO concentrations under anoxic and hyperoxic conditions, respectively.

In state of the art, the Clark type electrodes (U.S. Pat. No. 2,913,386) are commonly used to measure DO in aqueous solutions. This design comprises of a cathode and an anode submerged in an electrolyte and enclosed by a permeable membrane. Oxygen diffused through the membrane from the measured aqueous medium is reduced on the cathode surface. The electric current generated, exhibiting a linear relationship to the dissolved oxygen concentration, is measured, and recorded. However, in this design, due to oxygen consumption at the cathode and diffusion of oxygen through the membrane, sufficient flow of aqueous medium is required for accurate DO measurement. Moreover, the oxygen diffusion across the membrane and hence the measurement is affected by factors including bacterial growth, contamination of oil, organic matters, contaminants, and polymers in water. This leads to a decrease in diffusion rates. Further, over a period of time, membranes and electrolyte solution are deteriorated and therefore needs replacement. Furthermore, in this design, frequent servicing, calibration and refurbishing of the sensors are required.

Another type of dissolved oxygen sensor which is commonly used in medical and veterinary practices is an optical and polarographic sensor. Typically, in this design, luminescence-based optode or optical sensors with a pair of blue and red light-emitting diodes (LEDs) and a silicone photodetector are used. Oxygen in blood is monitored by percentage of haemoglobin in blood that carries oxygen using an electronic processor and a pair of light-emitting diodes (LEDs) of different wavelength, facing a photodiode through a translucent part of the patient's body (e.g., fingertip or earlobe). Absorption of light at different wavelengths is related to oxygen level of blood and the amount of transmittable light of different wavelengths is measured and related to oxygen levels in blood based on the Beer-Lamberts law.

Another known method of dissolved oxygen measurement in ultra-high purity fluid is disclosed by U.S. Pat. No. 9,541,539 B2. This method uses a window of optically transparent materials mounted in a fluid flow path, with an existing light source and a reference light source on one side, and a luminophore on the other side. The light emitted by the luminophore is measured, transmitted, and recorded by optical sleeve encasing in the sensor. However, in this method, the fluid must be of ultra-high purity otherwise the light transmission and hence the result is highly distorted, making field measurement and also some laboratory measurements impractical.

Further, in the existing art, oxidation of polyaromatic hydrocarbons (e.g., anthracene and rubene) by singlet oxygen is well known (Accounts of Chemical Research, 1968, 1, 104-110), and anthracenyl and rubenyl derivatives used as the singlet oxygen traps under controlled environments. However, the singlet oxygen generator, together with a singlet oxygen trap, must be dissolved in a solution for the reaction to occur. The chemical may also react with other ROS in the medium (e.g. OH radical, RO radical etc.). This prevents its use for DO measurement in open or natural system since the solution carrying the singlet oxygen generator and the oxygen trap may be interfered by physical and chemical factors prevailing in the external aqueous medium.

Despite dissolved oxygen measurements and designs of the above known techniques are simple and straightforward, these existing methods/designs present several problems in field measurement. First, spatial and temporal variations of dissolved oxygen are typically large. For example, at the same site, dissolved oxygen can vary from supersaturated (e.g. in the morning when photosynthetic activity is strong) to lack of oxygen (e.g. in dawn when oxygen is used up by respiration in the absence of replenishment from photosynthesis during darkness). Even within a small area, dissolved oxygen at different sites can be affected by water current pattern.

Dissolved oxygen variations are especially marked in eutrophic waters where oxygen level (especially oxygen depletion) is of major environmental concern. Also, vertical stratification of water bodies often leads to oxygen depletion in bottom water, despite dissolved oxygen is high in surface water. Due to different water circulation patterns, large spatial variations of dissolved oxygen are often found. Because of the above factors, frequent or continuous dissolved oxygen measurements are often necessary to cover these significant temporal and spatial variations (e.g. measurements of dissolved oxygen in surface, mid and bottom waters at different sites over a 24 hour cycle) which is often impractical or cost ineffective, especially in remote areas (e.g. open oceans).

To overcome the above problem, oxygen sensors may be installed on floating buoys and deployed at the remote sites, and signals collected by the oxygen sensors may be transmitted from the remote site using remote sensing technology. However, the high cost of such set up does not allow measurements over large areas. Furthermore, fouling problems caused by microbial organisms and larvae of aquatic animals (e.g. barnacles, serpulid worms, and mussels) growing on the permeable membrane of the oxygen electrodes will reduce gas diffusion and hence affect dissolved oxygen measurement. To alleviate these problems, regular change or cleanup of permeable membrane is often required, which again, impose practical problems for regular/continuous dissolved oxygen measurements in remote areas.

Furthermore, in most DO measurement and monitoring, the occurrence and duration of hypoxia (dissolved oxygen <2.8 mg $O_2$ $L^{-1}$) as well as the lowest dissolved oxygen value are the major concerns. The hypoxia may result in several environmental problems such as fish kill, reproductive and growth impairments and abnormal development of aquatic animals, anaerobic activities, and production of toxic gas such as $H_2S$. The existing oxygen sensors can provide such information only if the dissolved oxygen is measured for 24 hours. Obviously, this is not practical in many circumstances, especially in remote areas, or over large areas. Most of the devices fail to determine an appropriate oxygen level at different environmental conditions and over long period of time, and may lead to erroneous conclusions.

Thus, there is a long-felt need in the art for more sophisticated, programmable, yet simple to use apparatus, system, sensing device and method for determining dissolved oxygen level.

SUMMARY

This summary is provided to introduce concepts related to dissolved oxygen sensor(s), apparatus(es), and method(s) for determining dissolved oxygen content and the concepts are further described below in the detailed description. This summary is not intended to identify essential features of the claimed subject matter nor it is intended for use in determining or limiting the scope of the claimed subject matter.

In one implementation, a dissolved oxygen sensor for determining a dissolved oxygen content of a submerged medium is disclosed. The dissolved oxygen sensor may include at least a photo-oxidizable compound.

In some embodiments, the photo-oxidizable compound may be deposited on a solid support surface by a solution process selected from at least one of drop casting, spin coating, and covalent attachment. The solid support surface may be selected from at least one of a glass, a plastic, and a polymer.

In some embodiments, the photo-oxidizable compound may change its luminescent properties based upon photo-oxidation.

In some embodiments, the photo-oxidizable compound is a derivative of anthracene selected from at least one of 9,10-dimethylanthracene, and 9-carboxymethyl-10-methylanthracene.

In some embodiments, the dissolved oxygen sensor may further include one or more interdigitated conducting electrode patterns separated by a distance of microns and etched over the solid support surface.

In some embodiments, the dissolved oxygen sensor may be coated with an adhesive film such as a polymer insulation film.

In some embodiments, the interdigitated conducting electrode patterns may be configured to store a record of an impedance response generated by the interdigitated conducting electrode patterns.

In some embodiments, the impedance response may be accordance with the content of the dissolved oxygen in a medium (hereinafter may be alternatively referred to as "media") in which the dissolved oxygen sensor is submerged.

In some embodiments, the interdigitated conducting electrode patterns may be capable of transmitting a dissolved oxygen content data derived from the impedance response to a user device.

In some embodiments, the dissolved oxygen content data may be transmitted to the user device via an electronic chip comprising a processor, an impedance analyzer, and a wireless transmission device such as a Bluetooth module.

In some embodiments, the interdigitated conducting electrode patterns may be configured to store a dissolved oxygen data in form of compounds of different oxidized forms or states having one or more properties of UV-VIS absorption, IR absorption, luminescent, electrochemical, or electrical conductivity.

In another implementation, a dissolved oxygen content determining apparatus is disclosed. The dissolved oxygen content determining apparatus may include a light irradiation source and the dissolved oxygen sensor. The dissolved oxygen content determining apparatus may further include a moving device. The moving device may be enabled for movement in translational or rotational direction. The light irradiation source may be mounted on the moving device. The dissolved oxygen content determining apparatus may include a window at an edge portion of moving device. In some embodiments, the window at the edge portion of the moving device may be configured for fixing an optical path between the light irradiation source and the dissolved oxygen sensor positioned at the edge portion of the moving device. In some embodiments, the light irradiation source may be configured to control a time and light irradiation of the dissolved oxygen sensor.

In yet another implementation, a method for determining dissolved oxygen content in a media is disclosed. The method may include a step of submerging a moving device comprising a dissolved oxygen sensor in the media. The method may further include a step of fixing an optical path between a light irradiation source and the dissolved oxygen sensor through a window at an edge portion of the moving device. The method may further include a step of controlling a time and light irradiation of the dissolved oxygen sensor by a light irradiation source at a central portion of the moving device. The method may further include a step of irradiating a photo-oxidizable compound deposited over a solid support surface of the dissolved oxygen sensor by photo-oxidation using the light irradiation source. Further, the method may include a step of determining the dissolved oxygen content of a media based upon the irradiation of the photo-oxidizable compound deposited over a solid support surface of the dissolved oxygen sensor.

In some embodiments, the medium may be selected from, but are not limited to, a media such as an air media, an aqueous media, a liquid sample, a body fluid sample, a blood sample, or any biological sample.

In some embodiments, the method may further include a step of transmitting a data of quantified dissolved oxygen content to a user device through an electronic device such as a wireless transmission device integrated with the dissolved oxygen sensor.

In some embodiments, the step of quantifying the dissolved oxygen content may be performed on the basis of a formation of chemical compounds of different oxidized forms in the dissolved oxygen sensor. In some embodiments, the formation of chemical compounds of different oxidized forms is in correlation with one or more dissolved oxygen concentrations in the media, wherein the time and intensity of photooxidation of the photo-oxidizable compound is used to record the dissolved oxygen content data.

BRIEF DESCRIPTION OF THE DRAWINGS

The detailed description is described with reference to the accompanying figures. In the figures, the left-most digit(s) of a reference number identifies the figure in which the reference number first appears. The same numbers are used throughout the drawings to refer like features and components.

FIG. 7(*b*) illustrates a solution process for fabrication of the dissolved oxygen sensor 204, in accordance with an embodiment of the present disclosure.

FIG. 8(*b*) illustrates a plot I/Io of dissolved oxygen sensor 204 comprising a film 401 of a photo-oxidizable compound deposited on a substrate 402 after irradiation of the slide in deionized water and artificial seawater for a fixed irradiation time under different DO concentrations, in accordance with an embodiment of the present disclosure.

FIG. 8(*c*) illustrates overlaid emission spectra of the dissolved oxygen sensor 204 comprising a film 401 drop casted with high concentration of the 9,10-dimethylanthracene, in accordance with an embodiment of the present disclosure.

DETAILED DESCRIPTION

Figure 1:
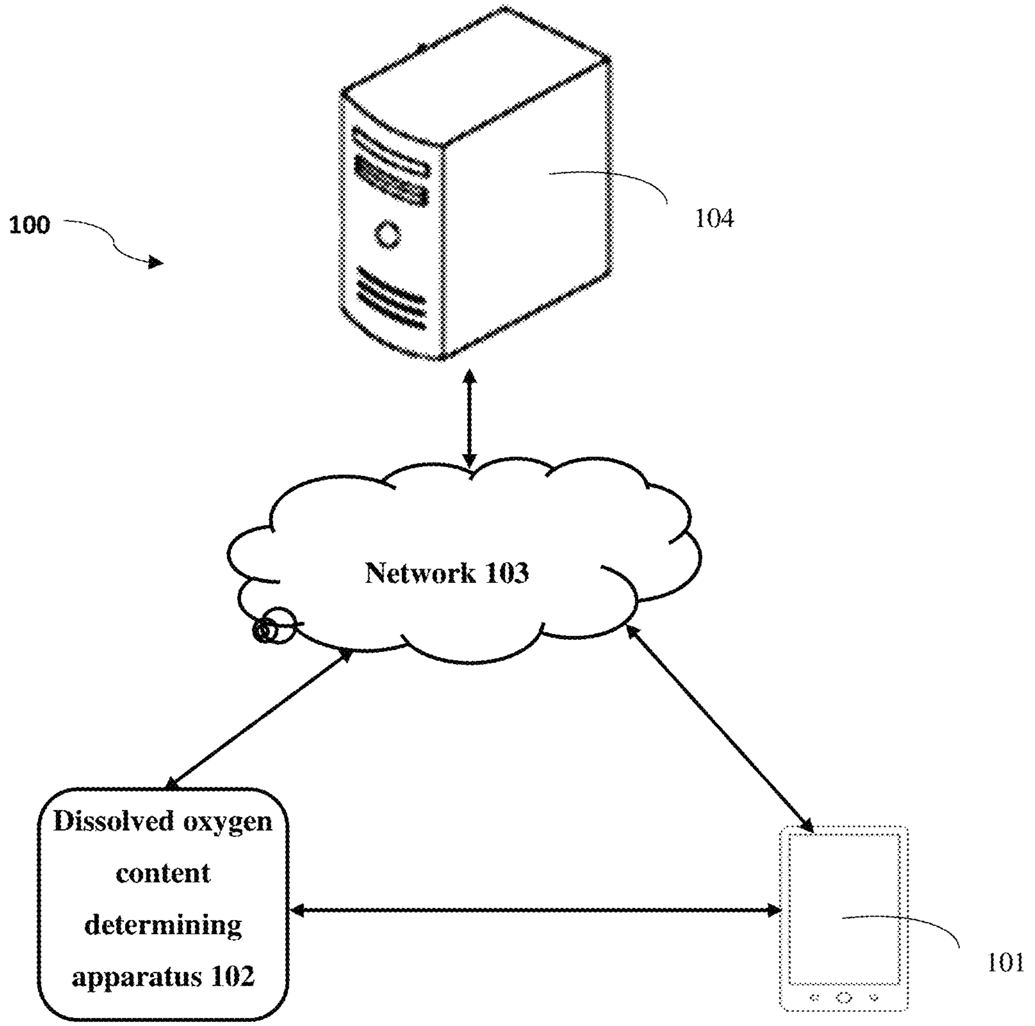
FIG. 1 illustrates a system 100 for determining dissolved oxygen content in a medium, in accordance with an embodiment of the present disclosure.

Reference throughout the specification to "various embodiments," "some embodiments," "one embodiment," or "an embodiment" means that a particular feature, structure, or characteristic described in connection with the embodiment is included in at least one embodiment. Thus, appearances of the phrases "in various embodiments," "in some embodiments," "in one embodiment," or "in an embodiment" in places throughout the specification are not necessarily all referring to the same embodiment. Furthermore, the particular features, structures or characteristics may be combined in any suitable manner in one or more embodiments.

The words "comprising," "having," "containing," and "including," and other forms thereof, are intended to be equivalent in meaning and be open ended in that an item or items following any one of these words is not meant to be an exhaustive listing of such item or items or meant to be limited to only the listed item or items.

It must also be noted that, the singular forms "a," "an," and "the" include plural references unless the context clearly dictates otherwise. Although any methods similar or equivalent to those described herein can be used in the practice or testing of embodiments of the present disclosure, the exemplary methods are described. The disclosed embodiments are merely exemplary of the disclosure, which may be embodied in various forms.

Now referring to FIG. 1, a system 100 for facilitating determination of dissolved oxygen content in a medium 301 (hereinafter may be alternatively referred to "test media") is illustrated in accordance with an embodiment of the present disclosure. The system may comprise a server 104, a network 103, a user device 101 and a dissolved oxygen content determining apparatus 102 communicatively coupled with the user device 101. The dissolved oxygen content determining apparatus 102 may be configured to register and transmit data recorded for determining the dissolved oxygen content in a medium, the details of which will be explained later in the subsequent paragraphs. In one implementation, the server 104 may be implemented in a cloud computing environment.

In one embodiment, one or more user devices may be collectively referred to as the user device 101 hereinafter. Examples of the user device 101 may include, but are not limited to, a portable computer, a personal digital assistant, a handheld device, and a workstation. The user devices 101 are communicatively coupled to the server 104 through a network 103.

In one embodiment, the network may be a wireless network, a wired network, or a combination thereof. The network can be implemented as one of the different types of networks, such as intranet, local area network (LAN), wide area network (WAN), the internet, and the like. The network may either be a dedicated network or a shared network. The shared network represents an association of the different types of networks that use a variety of protocols, for example, Hypertext Transfer Protocol (HTTP), Transmission Control Protocol/Internet Protocol (TCP/IP), Wireless Application Protocol (WAP), and the like, to communicate with one another. Further the network may include a variety of network devices, including routers, bridges, servers, computing devices, storage devices, and the like.

Figure 2:
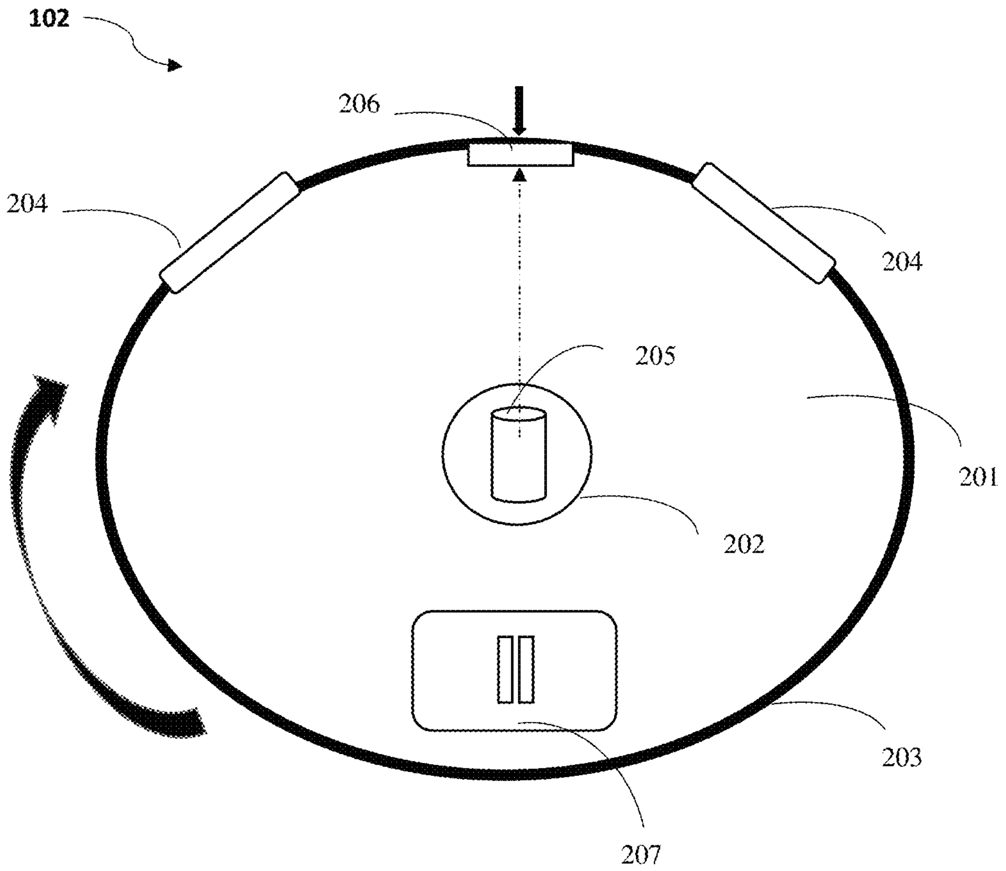
FIG. 2 illustrates a dissolved oxygen content determining apparatus 102, in accordance with an embodiment of the present disclosure.

Now, referring to FIG. 2, a dissolved oxygen content determining apparatus 102 is illustrated, in accordance with an embodiment of the present disclosure. In one embodiment, the dissolved oxygen content determining apparatus may include a moving device 201. In one embodiment, the moving device 201 may be enabled for movement in translational or rotational direction. The translational movement may be either in a horizontal direction or a vertical direction. Further, the rotational motion may be either a clockwise rotation or an anti-clockwise rotation. Therefore, it must be noted herein that although the description of the moving device 201 hereinafter is provided considering the moving device 201 is configured to operate as "a rotating device 201", however, the scope of the present claimed subject matter is not limited to enable movement of the moving device 201 in rotational direction but also in the translational direction.

In one embodiment, the rotating device 201 may be a rotating drum having a central portion 202 and an edge portion 203. In one embodiment, the speed and frequency of the rotating device 201 may be adjustable and further driven and/or controlled either mechanically or by an electronic device. In one embodiment, the speed and frequency of the rotating device 201 may be adjusted based on the number of measurements desired within a given time period. The rotation of the rotating device may be powered by electric, electronic, air flow, liquid flow, or mechanical power source devices.

The dissolved oxygen content determining apparatus 102 may further include a dissolved oxygen sensor 204 positioned at the edge portion 203 of the rotating device 201, a light irradiation source 205 mounted at the central portion 202 of a rotating device 201, a window 206 at the edge portion 203 of the rotating device 201, and an impedance analyzer circuit 207.

In one embodiment, the impedance analyzer circuit 207 may be placed at any position in the dissolved oxygen content determining apparatus 102. In another embodiment the impedance analyzer circuit 207 may be mounted to the dissolved oxygen sensor 204. The light irradiation source 205 may be placed at the central portion 202 independent from the edge portion 203 of the rotating device.

Figure 3:
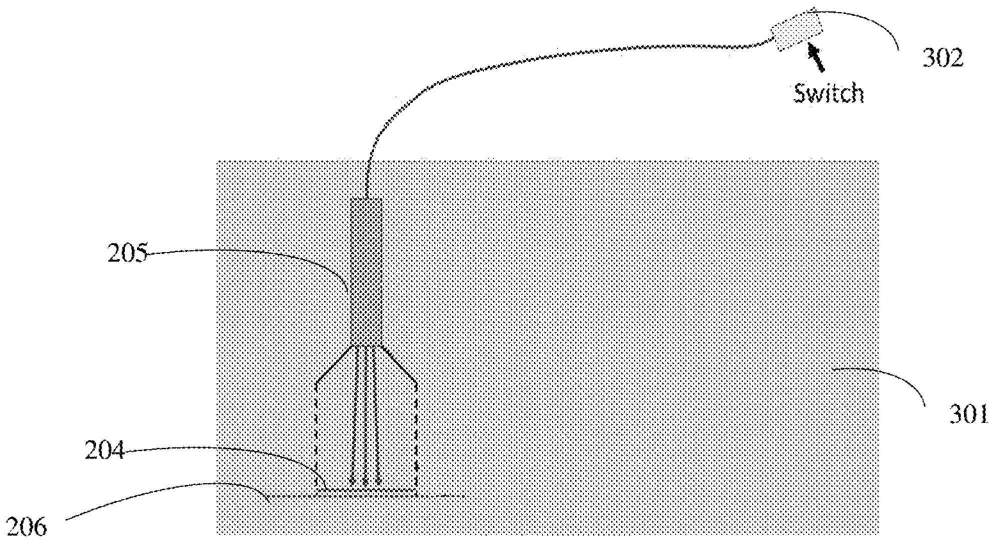
FIG. 3 illustrates a fixed path of the light irradiation source 205 passing through a medium 301 and through a window 206 to irradiate the dissolved oxygen sensor positioned inside the window 206, in accordance with the embodiment of the present disclosure.

In one embodiment, referring to FIGS. 2 and 3, the light irradiation source 205 may be at least one of a light emitting diode, Luminescence-based optodes, a red light-emitting diode, and a blue light-emitting diode. The direction of light emitted by the light irradiation source 205 (hereinafter may be interchangeably referred to as "LED light source") may be adjusted to pass through the medium 301 to be tested and then the window 206 at the edge portion 203 of the rotating device 201. The light emitted by the light irradiation source 205 may be further configured to photo-oxidize a chemical film of the dissolved oxygen sensor 204 at the window 206. It is to be noted herein that, the window 206 at the edge portion 203 of the rotating device 201 is for fixing an optical path between the light irradiation source 205 and the dissolved oxygen sensor 204 positioned at the edge portion 203 of the rotating device 201.

Figure 4:
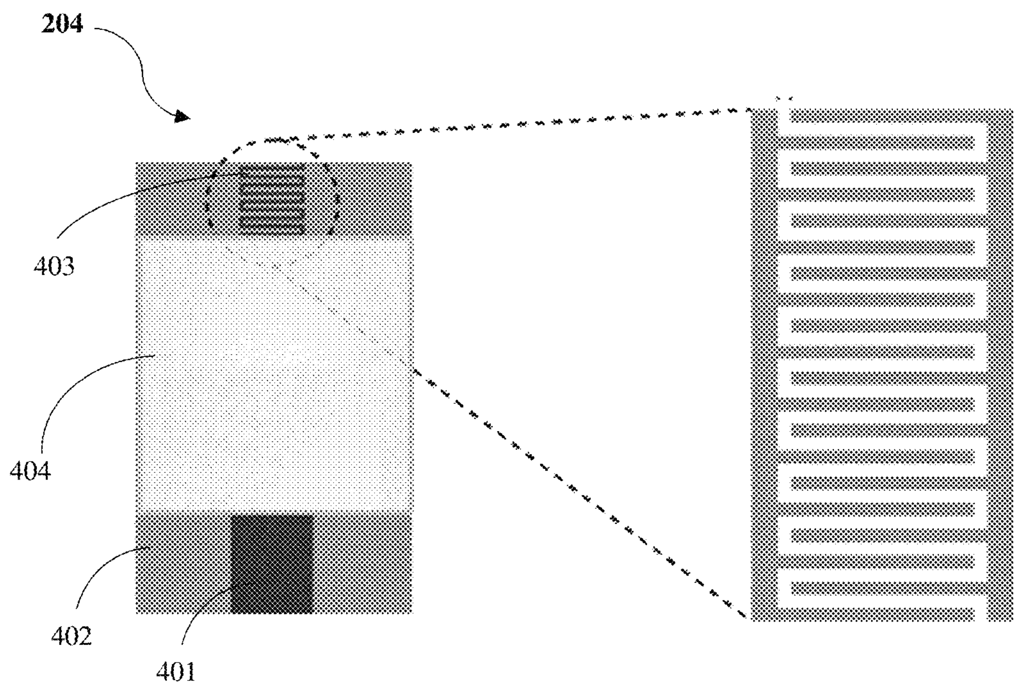
FIG. 4 illustrates construction of a dissolved oxygen sensor 204 for determining and quantifying a content of dissolved oxygen, in accordance with an embodiment of the disclosure.

Now referring to FIG. 4, a construction of dissolved oxygen sensor 204 for determining and quantifying a content of dissolved oxygen is depicted, in accordance with an embodiment of the present disclosure. The dissolved oxygen sensor 204 may include a film 401 comprising of one or more photo-oxidizable compounds deposited on a substrate 402. In one embodiment, the film 401 may a dissolved oxygen sensing film. In one embodiment, the dissolved oxygen sensor 204 may be configured to work when submerged in a medium 301. In one embodiment, the submerged medium may be a liquid medium selected from aqueous media, water, waste water, body fluid, blood, liquid, and biological sample. In another embodiment, the submerged medium may be gaseous media selected from, but are not limited to, air sample and gas mixture.

The dissolved oxygen sensor 204 may be configured to photo-oxidize the photo-oxidizable compounds comprised in the film 401 when irradiated with the light irradiation source 205. In one embodiment, the sensing compounds that are impregnated in the film 401 are not affected by the dynamics of the media.

In one embodiment, the dissolved oxygen sensor 204 may comprise a layer of interdigitated conducting electrode patterns 403 separated by distance of few microns and etched over the substrate 402 of the dissolved oxygen sensor 204. The dissolved oxygen sensor 204 may be coated with an adhesive film 404.

In one embodiment, the thickness of a conducting layer consisting of interdigitated conducting electrode patterns 403 may be in microns. The interdigitated conducting electrodes may be patterned and etched over the substrate 402. In one embodiment, the layer of interdigitated conducting electrode patterns 403 may be configured to store/register a record of dissolved oxygen in the medium 301 (test media shown in FIG. 3) as compounds having different oxidized forms or states having one or more properties including UV-VIS absorption, IR absorption, luminescent, electrochemical, and electrical conductivity. The interdigitated conducting electrode patterns 403 may be further connected to the impedance analyzer circuit 207.

Now, a method of coating the conducting layer of interdigitated conducting electrode patterns 403 is described in accordance with an embodiment of the present disclosure. In the first step, to coat the substrate 402, the dissolved oxygen sensor 204 may be spin coated or placed on a hot plate set to uniformly fix the active layer on the adhesive film. The active photosensitive material may be embedded into this soft polymer layer to form the film 401, more particularly the photosensitive film. In the next step, the dissolved oxygen sensor 204 may be slowly cooled down to room temperature. In one embodiment, an impedance spectroscopy may be carried out across the interdigitated electrodes. The impedance response of the dissolved oxygen may be measured using a potentiometric circuit of the impedance analyzer circuit 207. The frequency is swept in kHz to Hz region, with a peak-peak sine wave.

Figure 5:
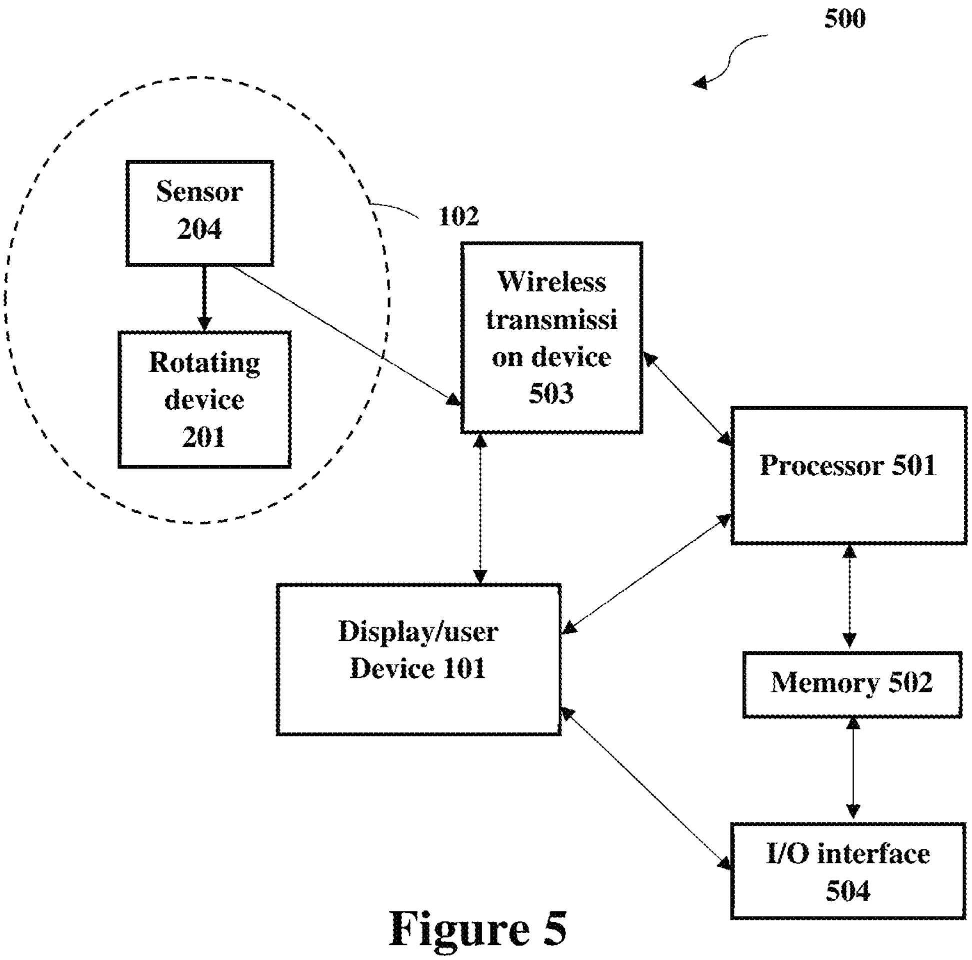
FIG. 5 illustrates a computer implemented system facilitating determination of dissolved oxygen using the dissolved oxygen determining apparatus 102, in accordance with an embodiment of the present disclosure.

In one embodiment, referring to FIGS. 4 and 5, the light irradiation source 205 may enable photo-oxidation of the film 401 comprising the photo oxidizable compound deposited on the substrate 402. The substrate 402 is positioned behind the window 206 to receive the irradiation from the light irradiation source 205 having a fixed light intensity for a fixed time. In an example, the substrate 402 positioned behind the window 206 may receive the irradiation from the light irradiation source 205 between 1-5 W of light intensity for 1-5 minutes. In one embodiment, the photo-oxidized form of a chemical on the film 401 formed after exposure to the light irradiation through water is enabled to be rotated to the next position where a signal is read by the impedance analyzer circuit 207 and transmitted in real time via network 103 using a wireless transmission device such as Bluetooth module to the user device 101.

In one embodiment, the dissolved oxygen sensor 204 may be configured to overcome the difficulties encountered by the known existing sensors such as oxygen diffusion, measurement of electric current, light transmission and Luminophore. The working of said dissolved oxygen sensor 204 is based on differential photo-oxidization of the film 401 of the photo-oxidizable compound deposited on the substrate 402. Furthermore, in the present disclosure, the dissolved oxygen level in the medium 301 is determined by establishing a correlation between the dissolved oxygen levels and the degree of photo-oxidation of the films impregnated with an active photo-oxidizable compound.

In one embodiment, the substrate 402 of the dissolved oxygen sensor 204 may be a solid support surface selected from at least one of a glass, a plastic, and a polymer, wherein the polymer may be selected from a polyethylene terephthalate, or a polyamide. The photo-oxidizable chemical over the film 401 is coated with an adhesive film 404. In one embodiment, the adhesive film 404 may be made of polyamide insulation film. In one embodiment, the photo-oxidizable compound is a derivative of anthracene selected from at least one of 9,10-dimethylanthracene, and 9-carboxymethyl-10-methylanthracene.

In an embodiment, by adjusting a fixed value of light intensity and irradiation time by the light irradiation source 205, the photooxidation of the active photo-oxidizable compound in the films such as anthracene derivatives may be correlated to level of dissolved oxygen in the medium such as an aqueous media. Since the reaction can only be reversed at higher temperatures such as at 80-100° C., the reaction is irreversible under any normal environmental, biological, and biomedical applications i.e., below 80° C. In still another embodiment, the irreversibility of the reaction occurring at the film 401 due to its photo-oxidizable property which may provide a permanent chemical record for the dissolved oxygen levels in the measured medium at a specific time (i.e. the time of irradiation). In the absence of irradiation, the film 401 may remain stable and the active compounds such as anthracene derivatives would not undergo oxidation. As such, the dissolved oxygen sensor and the relevant chemical reaction here disclosed are shielded from sunlight during deployment for DO measurement.

In one embodiment, the photo-oxidizable active compounds selected from at least one of the compounds enabled to show different and distinguishable absorption, luminescent, electrochemical, or electrical conductivity may be used in the fabrication of the film for dissolved oxygen measurements. In some embodiments, the photo-oxidizable compounds may change its luminescent properties based upon photo-oxidation. More particularly, anthracene derivative such as dimethylanthracene derivatives may be used to be photo-oxidized to form specific peroxides. As dimethylanthracene derivatives and their respective peroxides show different luminescent properties, the luminescent properties of films with dimethylanthracene derivatives may be used to estimate the dissolved oxygen level in the solution medium.

Now, again referring to FIG. 4, construction of the dissolved oxygen sensor 204 is depicted, in accordance with an embodiment of the present disclosure. In one embodiment, the dissolved oxygen sensor 204 may include the one or more interdigitated conducting electrode patterns 403 separated by distance of microns and etched over the substrate 402. The interdigitated conducting electrode patterns 403 may be configured to store/register a record of dissolved oxygen in the medium 301 (hereinafter interchangeably referred to as 'test media'). In one embodiment, the interdigitated conducting electrode patterns 403 may be configured to store/register a record of dissolved oxygen in the medium 301 for readout later or to be directly transmitted to the user device 101 via the network 103 in real time. In an embodiment, the dissolved oxygen sensor may be coated with the adhesive film 404.

In one embodiment, the dissolved oxygen sensor 204 may configured to use the two-interdigitated electrode structure of interdigitated conducting electrode patterns 403 to register and transmit the changes in the film 401 comprising of luminescent dimethylanthracene derivative in response to the dissolved oxygen level of the medium.

In one embodiment, a method for determining dissolved oxygen content in a media is disclosed in accordance with an embodiment of the present disclosure. The method may include a step of submerging a dissolved oxygen content determining apparatus 102 in a medium 301. The method may include a step of positioning the dissolved oxygen sensor 204 at the edge portion 203 of the rotating device enabling to move through the window 206. The method may further include a step of fixing an optical path between the light irradiation source 205 configured to pass through the medium 301, the window 206 and the dissolved oxygen sensor 204. The method may further include a step of controlling time and light irradiation intensity of the light irradiation source 205 positioned at a central portion of a rotating device. Further, the method may include a step of irradiating a photo-oxidizable compound deposited over a solid support surface of the dissolved oxygen sensor by photo oxidation using the light irradiation source. The method may further include transmitting a data of quantified dissolved oxygen content (i.e. a dissolved oxygen content data) to the user device 101 through a wireless transmission device integrated with the dissolved oxygen sensor 204.

In an embodiment, the quantification of the dissolved oxygen content of the medium 301 may performed on the basis of a formation of chemical compounds of different oxidized forms in the dissolved oxygen sensor 204. In one embodiment, the step of quantifying the dissolved oxygen content may be performed by means of photo-oxidation of the film 401 comprising of a photo-oxidizable compound. In one embodiment, the formation of chemical compounds of different oxidized forms is in correlation with one or more dissolved oxygen concentrations in the medium 301, and wherein the time and intensity of photooxidation of the photo-oxidizable compound is used to record the dissolved oxygen content data. Furthermore, the method may include displaying the dissolved oxygen content over the user device 101.

Referring to FIGS. 1 and 5, in one embodiment, the processor 501 (hereinafter may be alternatively referred to as central processing unit) may display the notification on the display of the system 100. In one embodiment, the notification may be displayed on the user devices 101. In another embodiment, the processor 501 may directly transmit notification to the one or more user device 101 using a wireless transmission device 503 or through the server 104.

Referring to FIG. 5, the components of computer implemented system 100 may include the processor 501, the user interface 504, a memory 502, modules such as the wireless transmission device 503, and data (not shown in figure). In one embodiment the processor 501 is configured to fetch and execute computer-readable instructions stored in the memory 502.

In an implementation the memory 502 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and memory cards. The memory 502 may include other modules and data.

In one embodiment, the data may comprise data repository and other data. The data repository may be configured to store the data processed, received, and generated by one or more of the modules. The other data may include data generated as a result of the execution of one or more modules.

Now, referring to FIGS. 1-5, the system 100 may include a user device 101, a dissolved oxygen content determining apparatus 102 further comprising a light irradiation source 205 mounted at a central portion 202 of a rotating device 201, a dissolved oxygen sensor 204 positioned at an edge portion 203 of the rotating device 201, an impedance analyzer circuit 207, a processor 501; and a memory 502 coupled to the processor 501. The processor 501 may be configured to execute a plurality of instructions stored in a memory 502. In one embodiment, the processor 501 may be implemented as central processing unit, referred as processor or CPU interchangeably.

In one embodiment, the processor may be implemented as one or more microprocessors, microcomputers, microcontrollers, digital signal processors, state machines, logic circuities, and/or any devices that manipulate signals based on operational instructions. Among other capabilities, the at least one processor is configured to fetch and execute computer-readable instructions stored in the memory.

In one embodiment, the impedance analyzer circuit 207 may be configured to measure an impedance response of the dissolved oxygen sensor in accordance with the content of dissolve oxygen in the test media. It must be noted herein that the impedance response of the dissolved oxygen sensor is in accordance with the content of dissolve oxygen in the test media in which the dissolved oxygen sensor is submerged.

Now referring to FIGS. 1, 2 and 4, the processor may detect whether the user device 101, has received information from, the dissolved oxygen sensor 204 comprising a Bluetooth module and the interdigitated conducting electrode patterns 403 connected externally or integrally to the dissolved oxygen sensor.

In one embodiment, the processor 501 may be configured for detecting whether the dissolved oxygen sensor 204 is placed at the edge portion 203 of the rotating device 201 at a predetermined position, wherein the rotating device 201 is submerged in the test medium 301. The processor 501 may be configured for performing, based upon detecting the position of dissolved oxygen sensor 204, one or more steps in accordance with embodiments of the disclosure. The processor 501 may be configured for fixing an optical path between the light irradiation source 205 and the dissolved oxygen sensor 204. The processor 501 may be configured for adjusting time and light irradiation intensity of the light irradiation source 205, quantifying the dissolved oxygen content of a test medium 301 by means of photo-oxidation of a film 401 of a photo-oxidizable compound incorporated in the dissolved oxygen sensor 204. The processor 501 may be configured for quantifying the dissolved oxygen content of a medium 301 by means of photo-oxidation of the film 401 of a photo-oxidizable compound incorporated in the dissolved oxygen sensor 204. The processor 501 may be further configured for transmitting a data of quantified dissolved oxygen content to the user device 101 through the wireless transmission device 503 integrated with the dissolved oxygen sensor 204. The processor 501 may be further configured displaying the dissolved oxygen content over the user device 101.

In an alternative embodiment, the processor 501 may be configured to execute a plurality of instructions stored in a memory for: transmitting a data of quantified dissolved oxygen content to the user device through the dissolved oxygen content determining device.

In one embodiment, the step of quantifying the dissolved oxygen content may be performed on the basis of the formation of chemical compounds of different oxidized forms and properties under different dissolved oxygen concentrations in the media, and wherein photooxidation of dimethyl anthracene is used to record the level of dissolved oxygen.

Figure 6:
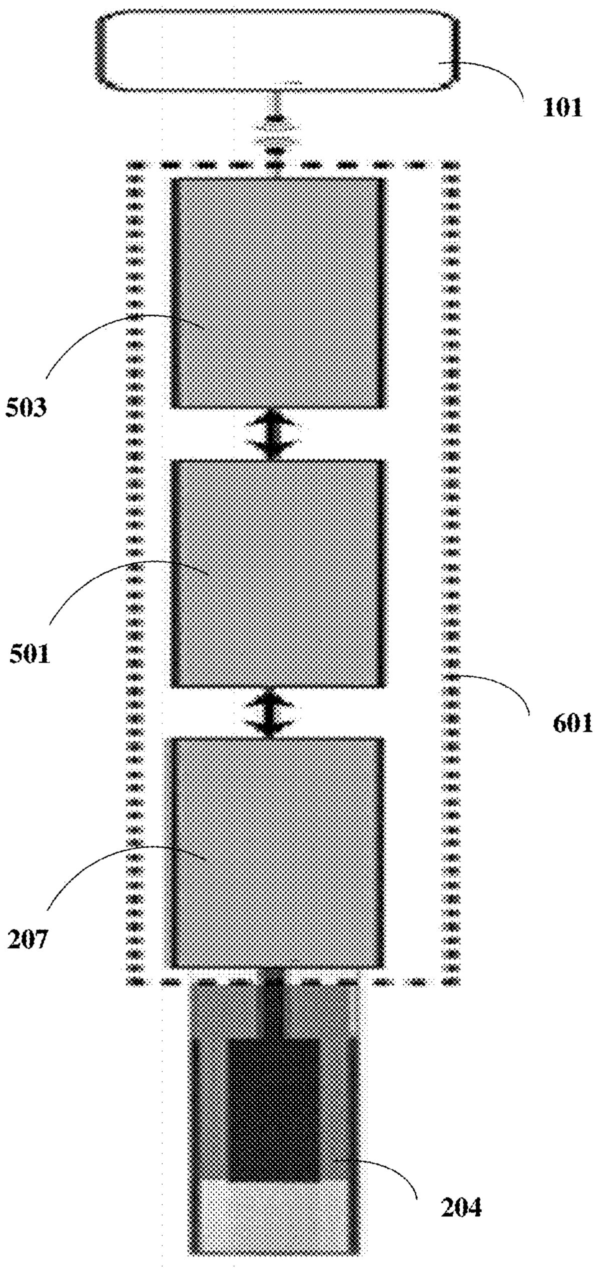
FIG. 6 illustrates an electronic chip 601 (also referred to as "E-card unit 601") integrated between a user device 101 and the dissolved oxygen determining apparatus 102, in accordance with an embodiment of the present disclosure.

In one embodiment, referring to FIG. 6, the dissolved oxygen sensor 204 may include a unit integrated or separately attached to the dissolved oxygen sensor 204 which is referred to as "E-card unit" 601 hereafter. In one embodiment, the E-card unit 601 may comprise the processor 501 (also referred to as CPU) which communicates with an impedance analyzer circuit 207. In one embodiment, the E-card unit 601 may be configured to communicate the results to the Bluetooth module. Further, the Bluetooth module may be configured to transmit the data to a user device 101 through the network 103. In one embodiment, the user device 101 may include a custom-built application to read and analyze the data received from the E-card unit 601.

In another embodiment, a method of fabrication of the dissolved oxygen sensor 204 is disclosed. In one embodiment, the method of fabrication of the dissolved oxygen sensor 204 may include a step of deposition of photo-oxidizable compound over a substrate by at least one of the process selected from drop casting, spin coating, and covalent attachment.

In one illustrative example of the method of fabrication of the dissolved oxygen sensor 204, the method may include a step of deposition of 9,10-dimethylanthracene and its derivative over the substrate 402 as a solid support substrate. The deposited layer of 10-dimethylanthracene and its derivatives is enabled to display strong luminescence and react with singlet oxygen to generate non-emissive endoperoxides when irradiated using a light irradiation source 205 as disclosed in scheme 1 below.

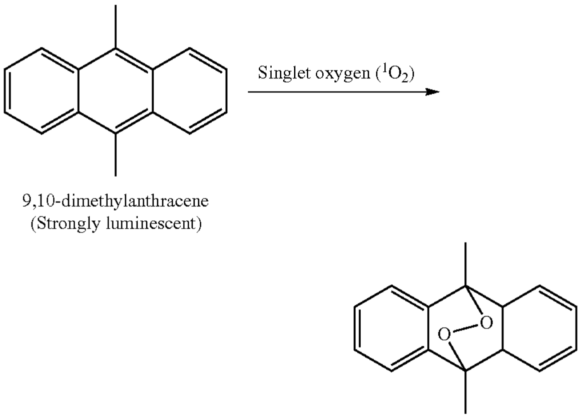

9,10-dimethylanthracene
(Strongly luminescent)

endoperoxide
(non-luminescent)

The photo-oxidizable anthracene derivative does not react with dissolved oxygen in its ground state (which is a triplet state of the oxygen). However, under UV irradiation the anthracene derivative such as dimethylanthracene derivatives on a surface of the film 401 serves as a photosensitizer and generates singlet oxygen, which react with the dimethylanthracene derivatives in the film matrix.

In one embodiment, formation of the oxidized form of the photo-oxidizable compound in the film 401 may be determined by recording change of the luminescent intensity upon UV irradiation with a fixed light intensity and time, which is correlated with the dissolved oxygen level of the immersed medium. Therefore, the dissolved oxygen levels of the medium such as an aqueous medium in which the dissolved oxygen content determining apparatus 102 (comprising a dissolved oxygen sensor 204 positioned at the edge portion 203 of the moving device 201) is immersed may be calculated based on correlation value of luminescent intensity and time.

In one embodiment, as the sensing capacity of the photo-oxidizable compound in the film 401 of the dissolved oxygen sensor 204 is only triggered by the light irradiation, the dissolved oxygen level is registered by the interdigitated conducting electrode patterns 403 at the predefined time and area of light irradiation. Referring to FIGS. 2 and 3, the time and intensity of the irradiation and the area of light excitation may be controlled by the light irradiation source 205 to determine the dissolved oxygen level of the medium 301 at any given time and recorded in the specific designated area of the dissolved oxygen sensor 204. The recorded result may not be affected by any subsequent change of DO levels in the medium.

In one embodiment, the dissolved oxygen sensor 204 based on the photo-oxidation principle with controlled excitation light intensity and irradiation time is fabricated as illustrated in FIGS. 3 and 4.

FIG. 3 illustrates a fixed path of the light irradiation source 205 passing through a medium 301 and through a window 206 to irradiate the dissolved oxygen sensor positioned inside the window 206, in accordance with the embodiment of the present disclosure.

The dissolved oxygen content determining apparatus 102 is submerged/immersed in the medium 301. The dissolved oxygen concentration in the medium 301 such as deionized water may be determined by quantifying the photo-oxidized product formed in the film 401 of the dissolved oxygen sensor 204 upon irradiation for a fixed period.

In another embodiment, based on the difference between luminescent properties of the active photo-oxidizable compound before and after photo-oxidation as quantified by emission spectroscopy, the content of the dissolved oxygen in the medium 301 is determined.

In yet another embodiment, the right irradiation source, the dissolved oxygen determining apparatus 102, the dissolved oxygen sensor 204, the rotating device 201 and a light irradiation source 205 are configured to be supplied with an electric power source and may be further operatable by utilizing a power switch 302.

Figure 7:
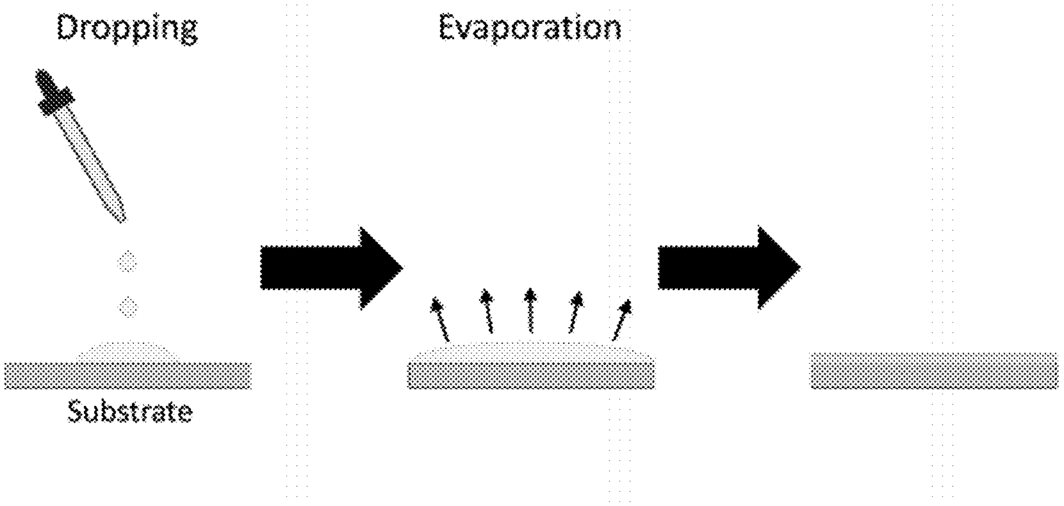
FIG. 7(*a*) illustrates a drop casting process for fabrication of the dissolved oxygen sensor 204, in accordance with an embodiment of the present disclosure.
Figure 7:
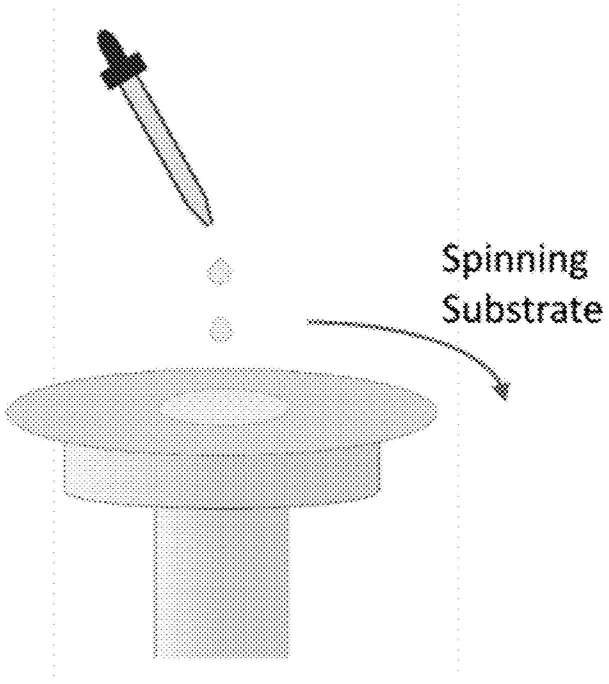

Referring to FIG. 7(*a*), an illustrative example of drop casting process for fabrication of the dissolved oxygen sensor 204 is depicted, in accordance with an embodiment of the present invention.

Now, referring to FIG. 7(*a*) and FIG. 4, the method of fabrication of the dissolved oxygen sensor 204 by drop-casting process is illustrated. In one embodiment, the film 401 is a physically-adsorbed neat film that can be fabricated by drop casting, which is done by dropping the solution of the active photo-oxidizable component on the surface and followed by slow evaporation. In one embodiment, the thickness of the film 401 deposited on the surface of the substrate 402 is proportional to the concentration of the solution prepared. Due to the variations of evaporation rate, the film thickness prepared by this method is less homogeneous.

In one embodiment, the method of fabrication of the dissolved oxygen sensor 204 by drop casting include a step washing of the substrate 402 with water and then methanol thrice. The method may further include a step of drying of the substrate 402 under vacuum prior to drop casting the film 401. In the next step, the film 401 (2.5 cm×2.5 cm) is prepared by drop casting of a solution of the sensing compound such as 9,10-dimethylanthracene (450 μL, 0.1 mM in toluene) on the substrate 402 made of flat glass surface. The glass slides of the substrate 402 were then dried in darkness for 12 hours by slow evaporation. The resulting glass slides of the substrate 402 comprising film 401 of, 10-dimethylanthracene which may be used as a light-triggered sensor, and more specifically as the dissolved oxygen sensor 204.

Figure 8:
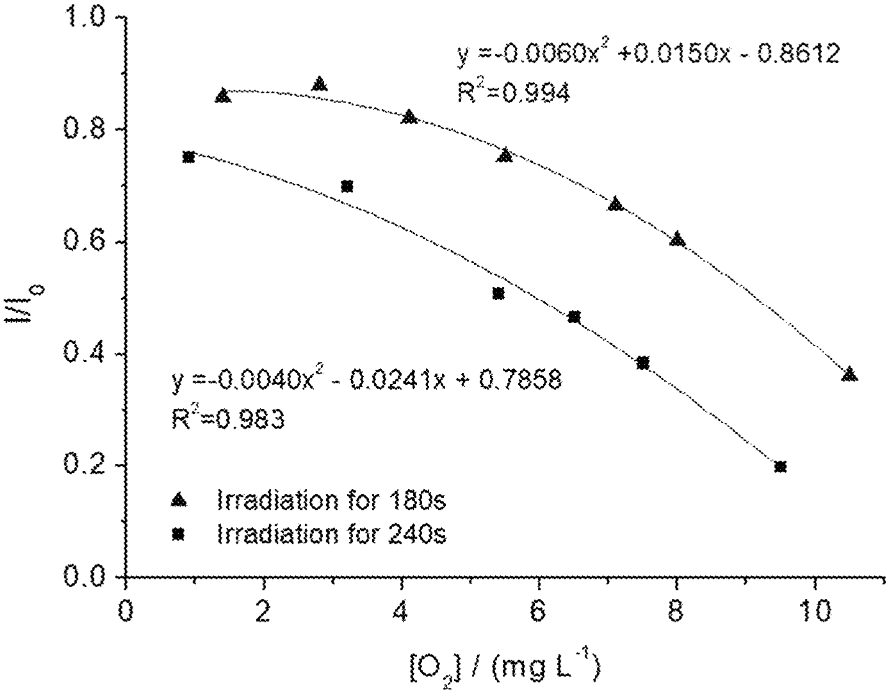
FIG. 8(*a*) illustrates a plot of $I/I_o$ of dissolved oxygen sensing of the dissolved oxygen sensor 204 after irradiation of the slide (film) 401 in deionized water for different time versus dissolved oxygen concentration, in accordance with an embodiment of the present disclosure.
Figure 8:
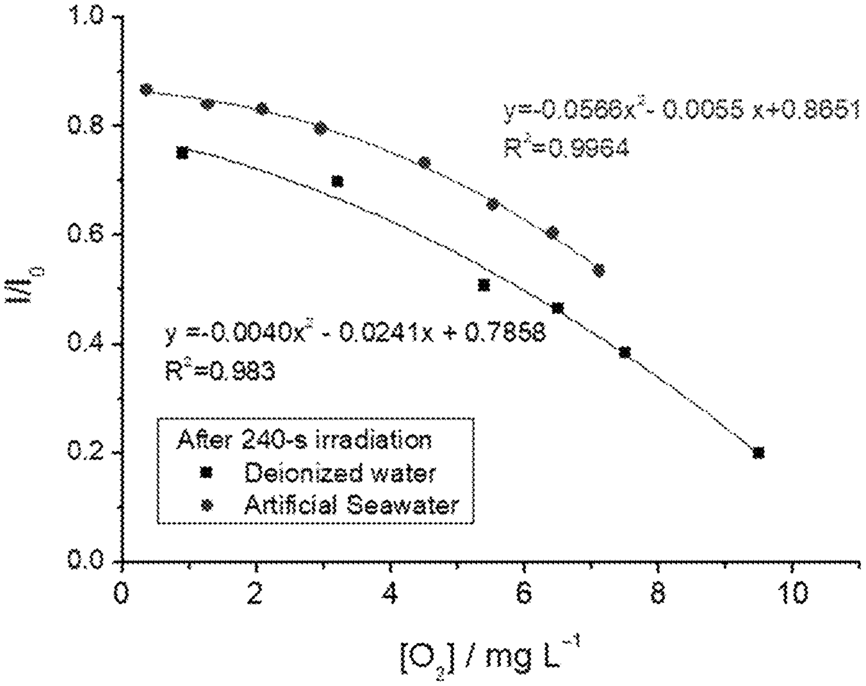
Figure 8:
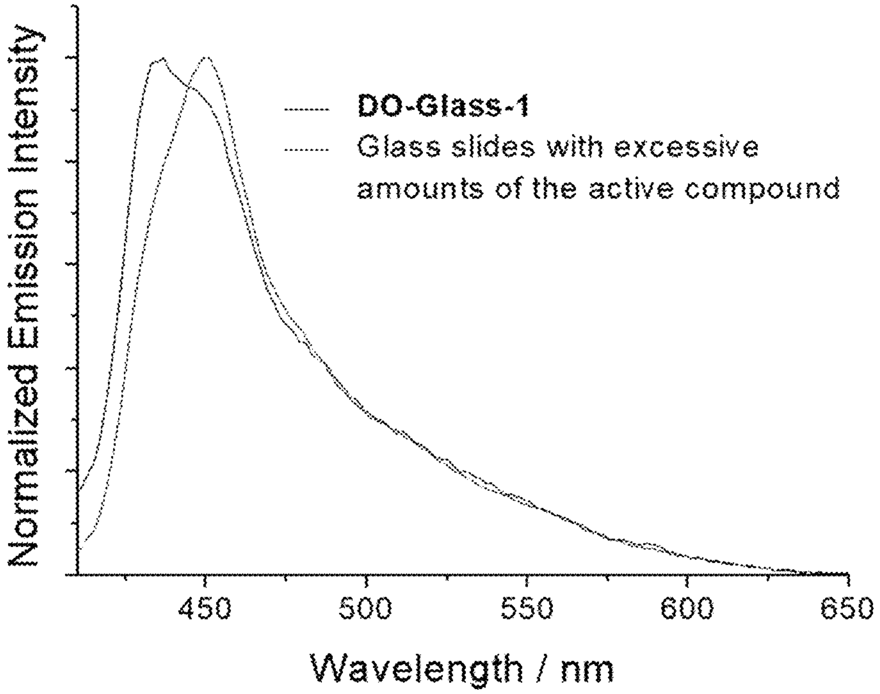

Referring to FIG. 8(*a*), a plot of $I/I_o$ of dissolved oxygen sensing of the dissolved oxygen sensor 204 after irradiation of the slide (film) 401 in deionized water for different time versus dissolved oxygen concentration is illustrated. It must be noted herein that, experimental results depicted that the intensity of fluorescence produced by 9,10-dimethylanthracene on film 401 decreased in response to irradiation, and the decrease in intensity of fluorescence is directly related to dissolved oxygen levels in the deionized water medium 301. FIG. 8(*a*) illustrates a plot of I/Io (Io and I are the emission intensity before and after irradiation, respectively) versus dissolved oxygen concentration in the medium, which determines that the decrease in fluorescence intensity of the photo-oxidizable chemical of the film 401 is directly related to dissolved oxygen level in the deionized water and also time of irradiation. The decrease of fluorescence intensity may be attributed to the photo-oxidation of the emissive 9,10-dimethylanthracene to non-emissive endoperoxide which is also related to oxygen concentration in the ambient environment. As a result, the degree of oxidation increases with both dissolved oxygen level of the solution and irradiation time. By quantifying the change of emission intensity of the film in the solution upon a fixed intensity and duration of irradiation, the dissolved oxygen level in the medium can be determined.

In another embodiment, referring to FIG. 8(*b*), a plot I/Io of dissolved oxygen sensor 204 comprising a film 401 of a photo-oxidizable compound deposited on a substrate 402 after irradiation of the slide in deionized water and artificial seawater for a fixed irradiation time under different DO concentrations is illustrated. Since dissolved oxygen measurement and determination in seawater is important, the validity of dissolved oxygen quantification of the dissolved oxygen sensor 204 comprising the film 401 of a photo-oxidizable compound deposited on a substrate 402 in artificial seawater was also evaluated. Similar to the results carried out in deionized water, the emission intensity of the slide in artificial seawater showed a similar decrease after irradiation, which was also directly related to the dissolved oxygen concentration, despite the relationship is slightly different from that found in deionized water (FIG. 8(*b*)), indicating calibration is required when the slide is used for DO quantification in different solution media.

Referring to FIG. 8(*c*) overlaid emission spectra of the dissolved oxygen sensor 204 comprising a film 401 drop casted with high concentration of the 9,10-dimethylanthracene is illustrated in accordance with an embodiment of the present invention. In one embodiment, glass slide (DO-Glass-1) is used as light-triggered dissolved oxygen sensor. Again, referring to FIG. 8(*c*) the amount of the active photo-oxidizable compound on the substrate 402 of the dissolved oxygen sensor 204 through the control of the concentration of the active compounds in the drop-casting because too much of the active compound would lead to aggregate formation and poor/insignificant luminescent responses after irradiation in water with different DO levels.

The aggregation formation of the active compound is characterized by the red-shifted emission spectra depicting photosensitivity of the film 401.

In one embodiment, FIG. 7(*b*) depicts an illustrative example of a method of fabrication of the dissolved oxygen sensor 204 by a solution process such as spin coating process in accordance with an embodiment of the present disclosure. In one embodiment, the film 401 is a spin coated film. In another embodiment, the spin coated film comprising a photo-oxidizable compound is fabricated as physically-adsorbed neat film. Compared with drop-casting, spin-coated films are more reproducible and homogeneous film. Different parameters, such as rate of rotation of the substrate, time for rotation, solution viscosity and concentration may be adjusted to fabricate film of different thickness in a controllable and consistent manner. A very thin film of 10 nm is fabricated using this method.

In yet another embodiment, a method of fabrication of the dissolved oxygen sensor 204 comprising a film 401 by covalent-attachment process is illustrated. In one embodiment, active compounds covalently attached on a solid substrate may be used to fabricate a stronger and more stable film. In order to covalently-functionalized the substrate 402 with functional compound (i.e. photo-oxidizable compounds for this application), anchoring functional groups suitable for covalently-linking on the solid surface have to be introduced through molecular design on the photo-oxidizable compound. On the other hand, modification of solid surface of the substrate 402 with active functional groups for covalent-attachment is also required.

In an illustrated example, method of fabrication of the dissolved oxygen sensor 204 by covalent-attachment process may include a step of silanization on glass surface of the substrate 402 with amine-substituted silianes such as (3-aminopropyl)-trimethoxysilane or treatment of polyester films such as polyethylene terephthalate (PET) with ethylenediamine or other structurally similar diamines to obtain an amino group functionalized surface. In one exemplary embodiment, environmental factors in the natural environment may only affect oxidation kinetics slightly and such small variations can be easily corrected by calibration curves.

The method fabrication of the dissolved oxygen sensor 204 by covalent-attachment process may be further described as below. For covalent attachment film, the solid supported surface of the substrate 402 was first functionalized with reactive functional groups such as amine to form the covalent linkage with a dissolved oxygen sensing compound such as 9-carboxymethyl-10-methylanthracene. For glass substrate, the amine functional group can be introduced by silanization with amine-containing silanes, such as (3-aminopropyl)trimethoxysilane (APTMS). For polyesters like polyethylene terephthalate (PET), amine functional group can be introduced to PET polymer chain by treatment with difunctionalized amine, such as ethylenediamine. Prior to covalent attachment, the amine functionalized PET film or glass was washed thrice with deionized (DI) water and acetone. The film 401 was dried by passing $N_2$ stream and then in vacuum oven at room temperature.

In one exemplary embodiment, a process of synthesis of dimethylanthracene derivative (9-carboxymethyl-10-methylanthracene) for covalent attachment on amine-functionalized surface is disclosed. The reaction was done under anhydrous conditions and strictly inert atmosphere using Schlenk technique. To a solution of 9,10-dimethylanthracene (500 mg, 2.42 mmol) in 6 mL THF cooled to −78° C. was added in a dropwise manner, lithium di-isopropylamide (2.0 M, 10 mL). The mixture was stirred for 2 hours at −78° C. After that, anhydrous carbon dioxide ($CO_2$) gas was bubbled into the solution for 1 hour. Thereafter, the reaction was quenched by a few drops of water. The solvent was removed under reduced pressure using rotary evaporator. 24 mL of THF/hexane (3:1 v/v) was added and extracted with 1 M sodium hydroxide solution (2×15 mL). The combined aqueous extract was then acidified by 3 M hydrochloric acid until pH<5 and then extracted with THF. After removal of the solvent and purification by column chromatography on silica gel using dichloromethane and then dichloromethane/acetone (1:1 v/v) as eluent, analytically pure compound was obtained. Yield: 60 mg (0.24 mmol, 10%). $^{1}$H NMR (400 MHz, $CDCl_3$, 298K) δ 8.37 (d, 2H), 8.28 (d, 2H), 7.57 (m, 4H), 4.69 (s, 2H), 3.13 (s, 3H). ESI-MS: m/z 249.5 $[M-H]^-$, 289.3 $[M+K]^+$. IR (KBr disc, v/$cm^{-1}$) 1697, 1425, 1225, 756.

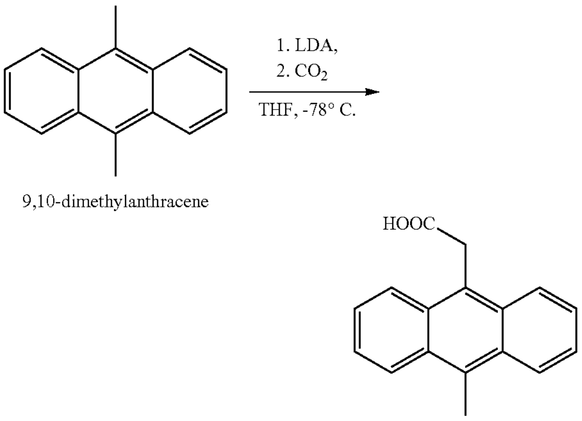

9,10-dimethylanthracene 9-carboxymethyl,10-methylanthracene

In another embodiment, a preparation method of activated ester solution for surface functionalization by covalent attachment is illustrated. A solution of an activated ester of 9-carboxymethyl-10-methylanthracene was first prepared for covalent attachment. This solution was prepared by the reaction of 3.13 mg of 9-carboxymethyl-10-methylanthracene in 0.4 mL N,N-dimethylformamide (DMF), 1.44 mg of N-hydroxysuccinimide (NHS) in 0.4 mL DMF and 2.58 mg of dicyclohexylcarbodiimide (DCC) in 0.1 mL of DMF. The reaction mixture in an anhydrous condition was stirred at room temperature under an inert atmosphere of nitrogen for 2 hours. Thereafter, 3.23 mg of N,N-diisopropylethylamine (DIPEA) was added into the reaction mixture and the solution is made up to a final volume of 2 mL.

In yet another embodiment a method of fabrication of a covalently-attached film on a PET based surface of the substrate 402 is disclosed. In one exemplary embodiment, step of addition an amine-functionalized PET film (5 cm×5 cm) to an activated ester solution (1 mL) was performed. The solution was left for 3 hours in the dark. Thereafter, the 9-carboxymethyl-10-methylanthracene functionalized film was washed thrice with DMF and then with methanol. After drying under nitrogen and vacuum, the resulting PET film of the dissolved oxygen sensor 204 is used as the light-triggered dissolved oxygen sensor.

Figure 9:
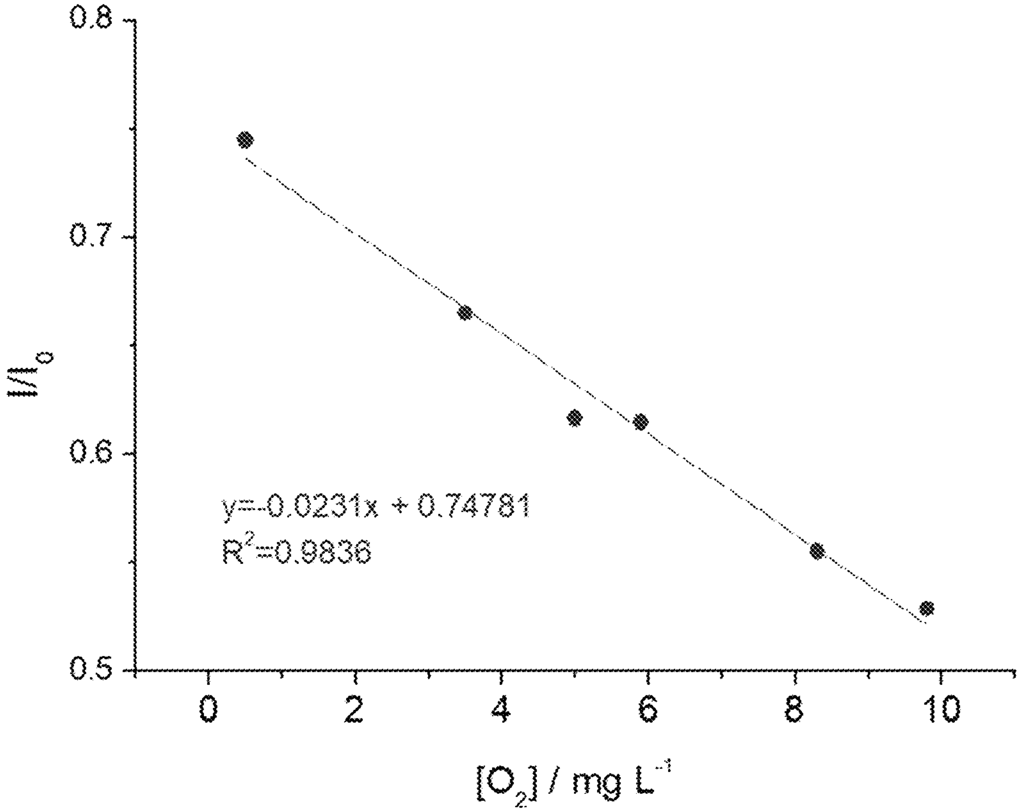
FIG. 9 illustrates a plot $I/I_o$ of dissolved oxygen sensor 204 comprising a polymer substrate as the substrate 402 after irradiation of the film 401 in deionized water for a fixed irradiation time versus different DO concentrations, in accordance with an embodiment of the present disclosure.

Now, referring to FIG. 9 a plot $I/I_o$ of dissolved oxygen sensor 204 comprising a PET based surface of the substrate 402 after irradiation of the film 401 in deionized water for a fixed irradiation time versus different DO concentrations is disclosed.

In one embodiment, referring to FIG. 9, determination of dissolved oxygen by the dissolved oxygen sensor 204 comprising the film 401 as a Covalently-attached film on PET based surface of the substrate 402 is illustrated. In one embodiment, by submerging the dissolved oxygen content determining apparatus 102 comprising the dissolved oxygen sensor 204 strip in water with different dissolved oxygen levels, evaluation is carried out. The dissolved oxygen in the medium 301 is determined based on the anthracene-based fluorescence of the film decrease in intensity after irradiation for a fixed irradiation time. As shown in the plot of I/Io versus dissolved oxygen concentration (FIG. 9), the response is observed almost linear. It is confirmed that the dissolved oxygen sensor 204 developed in this application can be used for dissolved quantification of the oxygen in the medium 301 such as aqueous media.

Figure 10:
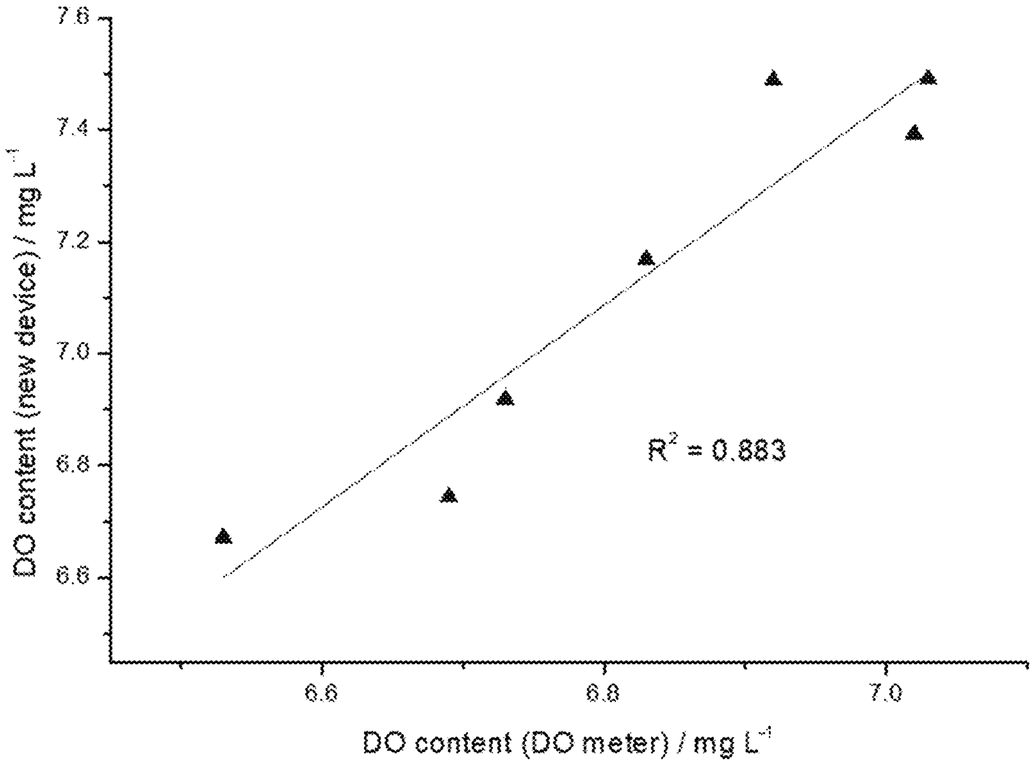
FIG. 10 illustrates a plot of dissolved oxygen content measured by dissolved oxygen content determining apparatus 102 comprising the dissolved oxygen sensor 204 in correlation with the dissolved oxygen content measured by Clark type electrode under field conditions.

Now, referring to FIG. 10, a plot of dissolved oxygen content measured by dissolved oxygen content determining apparatus 102 comprising the dissolved oxygen sensor 204 in correlation with the dissolved oxygen content measured by Clark type electrode under field conditions is illustrated. In one example, a field test of the dissolved oxygen content determining apparatus 102 was carried out to validate the laboratory findings reported above under natural conditions. Specifically, a set of dissolved oxygen content determining apparatus 102 comprising the dissolved oxygen sensor 204 was deployed 1.2 m and 3.6 m below seawater surface alongside with a Clarke type DO electrode. DO was measured using both of the dissolved oxygen content determining apparatus 102 and the Clarke type oxygen electrode over 4 hours, and the results obtained are those shown in FIG. 10. The field test results showed that DO values determined by the claimed invention are similar to, and also showed a significant correlation (See FIG. 10) with those measured by the Clarke type DO electrode.

The embodiments, examples and alternatives of the preceding paragraphs, the description, including any of their various aspects or respective individual features, may be taken independently or in any combination. Features described in connection with one embodiment are applicable to all embodiments unless such features are incompatible. Although implementations of the apparatus, system, sensor, and the method for determining dissolved oxygen content in a medium have been described in language specific to structural features and/or methods, it is to be understood that the appended claims are not necessarily limited to the specific features or methods described. Rather, the specific features and methods are disclosed as examples of implementations of apparatus, system, sensor, and the method for determining dissolved oxygen content in a medium.

What is claimed is:

1. A method for determining dissolved oxygen content in a medium, comprising:

submerging a moving device comprising a dissolved oxygen sensor in the medium such that the dissolved oxygen sensor is in contact with the dissolved oxygen content in the medium, wherein the dissolved oxygen sensor is positioned at an edge portion of the moving device;

fixing a light irradiation source at a central portion of the moving device which is independent from the edge portion of the moving device, thereby defining an optical path between a light irradiation source and the dissolved oxygen sensor through the medium;

controlling the irradiation source to irradiate the dissolved oxygen sensor at a predetermined wavelength for a predetermined period of time;

irradiating at least one photo-oxidizable compound deposited over a solid support surface of the dissolved oxygen sensor using the light irradiation source to facilitate generation of singlet oxygen, wherein an irradiation reacting with the at least one photo-oxidizable compound functions to convert the photo-oxidizable compound into a photosensitizer arranged to react with the dissolved oxygen in ground state to generate the singlet oxygen;

determining the dissolved oxygen content of the medium based upon the irradiation of the at least one photo-oxidizable compound, using the light irradiation source by irradiating the at least one photo-oxidizable compound using a UV irradiation source to generate the singlet oxygen in a presence of dissolved oxygen in the ground state in the medium, wherein the at least one photo-oxidizable compound is a derivative of anthracene selected from at least one of 9,10-dimethylanthracene, and 9-carboxymethyl-10-methylanthracene; and generating an impedance response on an interdigitated conducting electrode patterns disposed on the solid support surface, wherein the impedance response is in accordance with a content of the dissolved oxygen in the medium in which the dissolved oxygen sensor is submerged;

wherein the at least one photo-oxidizable compound is arranged to receive the irradiation from the light irradiation source having a predetermined light intensity for a predetermined time; and wherein the at least one photo-oxidizable compound changes its luminescent properties based upon a reaction with the singlet oxygen, and wherein the singlet oxygen is generated upon irradiation of the photo-oxidizable compound when the photo-oxidizable compound is in contact with the dissolved oxygen in the medium.

2. The method of claim 1, wherein the medium includes an air medium, an aqueous medium or a liquid sample.

3. The method of claim 1, wherein the step of determining the dissolved oxygen content is performed on the basis of a formation of chemical compounds of different oxidized forms of the at least one photo-oxidizable compound deposited over the solid support surface of the dissolved oxygen sensor.

4. The method of claim 3, further comprising transmitting a dissolved oxygen content data to a user device through a wireless transmission device integrated with the dissolved oxygen sensor.

5. The method of claim 4, wherein the formation of chemical compounds of different oxidized forms of the at least one photo-oxidizable compound is in correlation with one or more dissolved oxygen concentrations in the medium.

6. The method of claim 1, wherein the photo-oxidizable compound changes from luminescent to non-luminescent upon the reaction with the singlet oxygen being generated.

7. The method of claim 1, further comprising a step of transmitting dissolved oxygen content data to a user device via an electronic device comprising a processor, an impedance analyzer, and a wireless transmission device.

* * * * *